(12) United States Patent
Kusuura

(10) Patent No.: US 8,232,111 B2
(45) Date of Patent: Jul. 31, 2012

(54) MICROPIPETTE, MICROPIPETTE SYSTEM, AND METHOD FOR USING MICROPIPETTE

(75) Inventor: Takahisa Kusuura, Kawasaki (JP)

(73) Assignee: Empire Technology Development LLC, Wilmington, DE (US)

( * ) Notice: Subject to any disclaimer, the term of this patent is extended or adjusted under 35 U.S.C. 154(b) by 94 days.

(21) Appl. No.: 12/665,434

(22) PCT Filed: Jan. 29, 2009

(86) PCT No.: PCT/JP2009/051431
§ 371 (c)(1),
(2), (4) Date: Apr. 19, 2010

(87) PCT Pub. No.: WO2010/086977
PCT Pub. Date: Aug. 5, 2010

(65) Prior Publication Data
US 2011/0159606 A1 Jun. 30, 2011

(51) Int. Cl.
*G01N 1/10* (2006.01)
(52) U.S. Cl. ......... 436/180; 436/174; 422/520; 422/501
(58) Field of Classification Search ........................ None
See application file for complete search history.

(56) References Cited

FOREIGN PATENT DOCUMENTS

| JP | 05-184949 | 7/1993 |
|---|---|---|
| JP | 05-184949 A | 7/1993 |
| JP | 2004-070101 | 3/2004 |
| JP | 2004-070101 A | 3/2004 |
| JP | 2005-348689 | 12/2005 |
| JP | 2006-234446 | 9/2006 |
| JP | 2007-217331 | 8/2007 |
| JP | 2008-142659 A | 6/2008 |

OTHER PUBLICATIONS

Banks, D. "General introduction to micromachining." Microengineering Technologies and How to Exploit Them (1997) 1/1-1/6.*
Fujishima, Akira et al. "Titanium dioxide photocatalysis." Journal of Photochemistry and Photobiology C (2000) 1 1-21.*
Hoshino, Kazunori et al. "Electrowetting-based pico-liter liquid actuation in a glass-tube microinjector." Sensors and Actuators A (2004) 114 473-477.*
Nagai, H. et al. "Micro optical switching valve system based on reversible wettability conversion." 7th International Conference on Minaturized Chemical and Biochemical Analysis Systems (2003) 927-930.*

(Continued)

*Primary Examiner* — Yelena G Gakh
*Assistant Examiner* — Christopher A Hixson
(74) *Attorney, Agent, or Firm* — Foley & Lardner LLP

(57) ABSTRACT

There is provided a micropipette, a micropipette system, and a method for using a micropipette system capable of accurately sucking a desired quantitative volume of liquid for measurement. A micropipette system comprises a micropipette 1 including a liquid-holding chamber 12 that holds a liquid for measurement sucked in by capillary action through an opening 11 provided at an end of the liquid-holding chamber 12, the liquid-holding chamber 12 having an inner surface on which a photocatalyst layer 13 exhibiting a hydrophilic property at the time of light irradiation is formed, irradiation means 2 for emitting light toward the photocatalyst layer 13, and control means 3 for controlling the range of the area irradiated with the light from the irradiation means 2 in accordance with a desired quantitative volume of the liquid for measurement.

7 Claims, 3 Drawing Sheets

OTHER PUBLICATIONS

Jones, T. B. et al. "Frequency-dependent electromechanics of aqueous liquids: electrowetting and dielectrophoresis." Langmuir (2004) 20 2813-2818.*

International Search Report for PCT/JP2009/051431 mailed Apr. 14, 2009.

Office Action for Japanese Patent Application No. 2009-540538 mailed Nov. 12, 2009 (English translation not readily available).

McSporran, N. et al., "Synthesis of undoped and Ni doped $InTaO_4$ photoactive thin films by metal organic chemical vapor deposition", Surface & Coatings Technology 201 (2007), 9365-9368.

Miyauchi, M. et al., "Photoinduced Hydrophilicity of Heteroepitaxially Grown ZnO Thin Films", J. Phys. Chem B (2005), 109, 13307-13311.

Mills, Andrew et al., "Characterisation of the Photocatalyst Pilkington Activ™: A Reference Film Photocatalyst?," Journal of Photochemistry and Photobiology A: Chemistry, vol. 160, Issue 3, Aug. 21, 2003, pp. 213-224.

Lim, Ho Sun et al., "UV Driven Reversible Switching of a Roselike Vanadium Oxide Film between Superhydrophobicity and Superhydrophilicity," Journal of American Chemical Society, vol. 129, 2007, pp. 4128-4129.

Saito, T.K. et al., "Photocatalyst Coated Capillary Increases Efficiency of Membrane Penetration Process of Microinjection," Proceedings of the 22nd Annual International Conference of the IEEE Engineering in Medicine and Biology Society, vol. 4, 2000, pp. 2819-2820.

International Preliminary Report on Patentability for International Application No. PCT/JP2009/051431, The International Bureau of WIPO, Geneva, mailed on Aug. 9, 2011.

English language Abstract of WIPO Patent Publication No. 2005-348690 A, European Patent Office, espacenet database—Worldwide (2005).

* cited by examiner

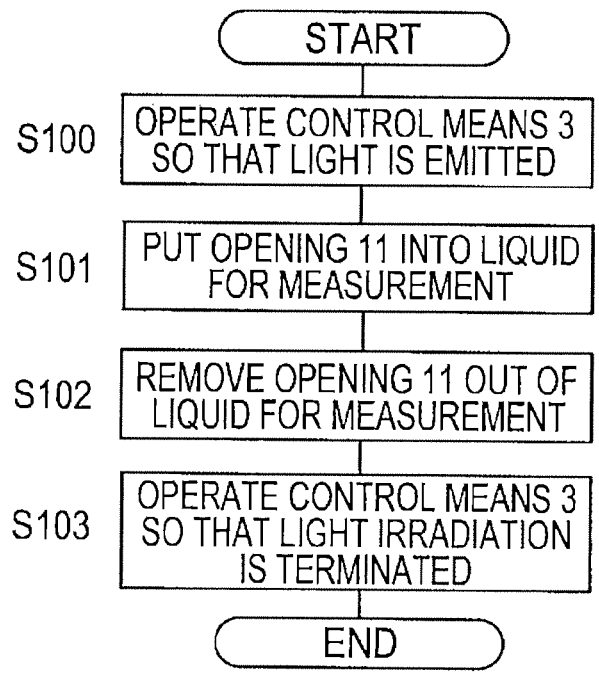
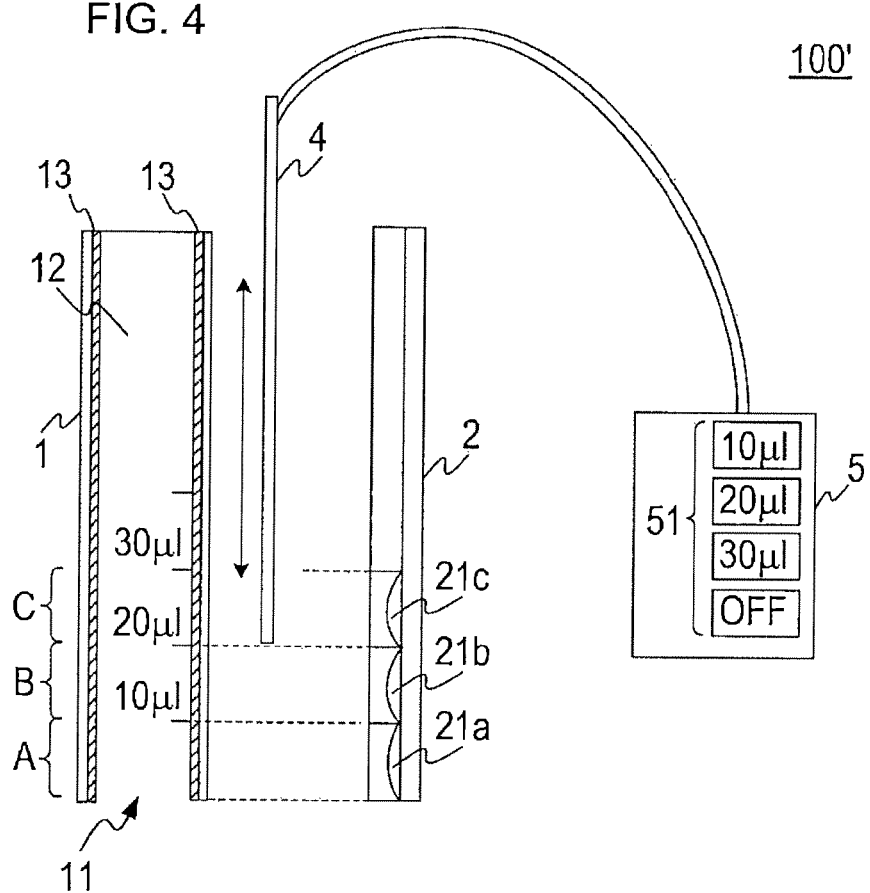

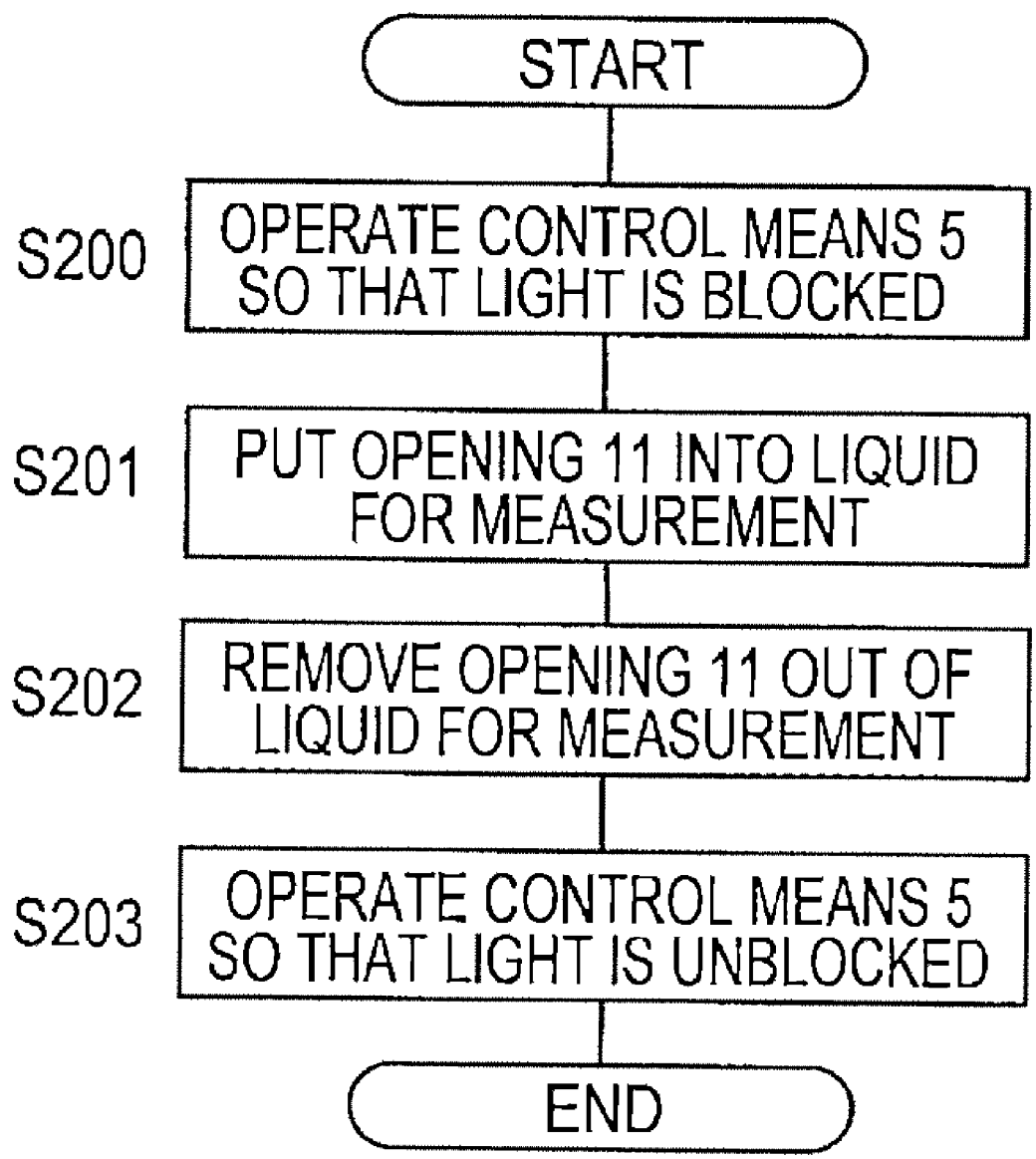

MICROPIPETTE, MICROPIPETTE SYSTEM, AND METHOD FOR USING MICROPIPETTE

CROSS-REFERENCE TO RELATED APPLICATIONS

The present application is a U.S. national stage application claiming the benefit of International Application No. PCT/JP2009/051431, filed on Jan. 29, 2009, the entire contents of which is incorporated herein by reference in its entirety.

TECHNICAL FIELD

The present disclosure relates to a micropipette, a micropipette system, and a method for using a micropipette.

BACKGROUND ART

In biochemistry and other similar fields, a micropipette has been used as a pipette for measuring a tiny volume of liquid on a micro-litter (μl) basis. A micropipette is typically used to measure a liquid for measurement in the following manner: A thin glass tube having an opening at one end thereof is put into the liquid for measurement, and the liquid for measurement is sucked into a liquid-holding chamber by capillary action. The micropipette stops sucking when the glass tube is removed out of the liquid for measurement, and a user reads markings provided on the micropipette to measure the liquid for measurement held in the liquid-holding chamber (see Patent Document 1, for example).

PRIOR ART DOCUMENT

Patent Document 1: Japanese Patent Laid-Open No. 05-184949

SUMMARY

The micropipette of related art is, however, problematic in that it is difficult to suck accurately a desired quantitative volume of liquid for measurement because the user himself/herself visually reads the measurement markings on the micropipette and stops the sucking of the liquid for measurement.

It is therefore desired to provide a novel micropipette, micropipette system, and method for using a micropipette system capable of solving the problem described above and accurately sucking a desired quantitative volume of liquid for measurement.

Means for Solving the Problems

A micropipette of the present disclosure comprises a liquid-holding chamber that holds a liquid for measurement sucked in by capillary action through an opening provided at an end of the liquid-holding chamber, the liquid-holding chamber having an inner surface on which a photocatalyst layer exhibiting a hydrophilic property at the time of light irradiation is formed.

A micropipette system of the present disclosure comprises the micropipette described above, irradiation means for emitting light toward the photocatalyst layer, and control means for controlling the range of the area irradiated with the light from the irradiation means in accordance with a desired quantitative volume of the liquid for measurement.

The liquid-holding chamber may have a circular tube-shaped structure in which the photocatalyst layer is formed along the inner-diameter surface of the liquid-holding chamber and an end of the liquid-holding chamber is open as the opening. Alternatively, the liquid-holding chamber may have a rectangular tube-shaped structure in which the photocatalyst layer is formed along the inner surface of the liquid-holding chamber and an end of the liquid-holding chamber is open as the opening.

Another micropipette system of the present disclosure may comprise the micropipette described above and light blocking means for blocking light toward the photocatalyst layer, and may further comprise control means for controlling the range over which the light blocking means blocks light in accordance with a desired quantitative volume of the liquid for measurement.

Another micropipette system of the present disclosure may comprise the micropipette described above and irradiation means for emitting light toward the photocatalyst layer, and the irradiation means may be provided integrally with the micropipette along the direction in which the liquid for measurement is sucked into the micropipette.

A method for using a micropipette of the present disclosure is a method for using a micropipette including a liquid-holding chamber that holds a liquid for measurement sucked in by capillary action through an opening provided at an end of the liquid-holding chamber, the liquid-holding chamber having an inner surface on which a photocatalyst layer exhibiting a hydrophilic property at the time of light irradiation is formed, the method comprising emitting light toward the photocatalyst layer to change the state of the photocatalyst layer to the hydrophilic state, and sucking the liquid for measurement in by capillary action and holding the sucked liquid.

The method for using a micropipette of the present disclosure may further comprise blocking the light emitted toward the photocatalyst layer to change the state of the photocatalyst layer to a hydrophobic state, and dispensing the held liquid for measurement through the opening.

BRIEF DESCRIPTION OF THE DRAWINGS

FIG. 3 is a flowchart showing processes performed by the micropipette system 100 of the first embodiment;

FIG. 4 is a schematic view showing a micropipette system 100' of a second embodiment; and FIG. 5 is a flowchart showing processes performed by the micropipette system 100' of the second embodiment.

DESCRIPTION OF SYMBOLS

Figure 1:
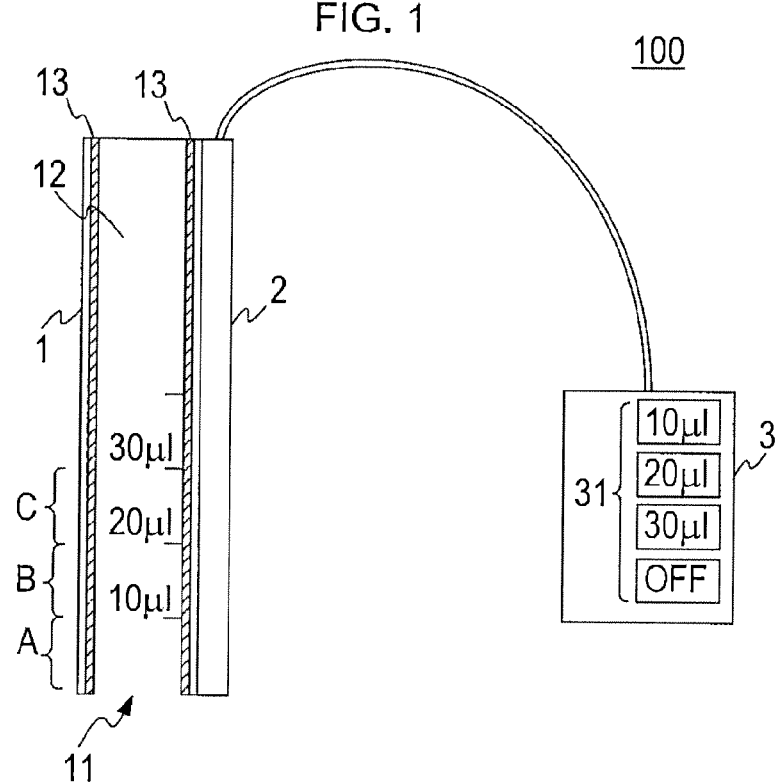
FIG. 1 is a schematic view showing a micropipette system 100 of a first embodiment.

1 micropipette
2 irradiation means
3, 5 control means
4 light blocking means
11 opening
12 liquid-holding chamber
13 photocatalyst layer
100, 100' micropipette system

DETAILED DESCRIPTION

Preferred embodiments for carrying out the present disclosure will be described below with reference to the drawings. It is noted that the size, the positional relationship, and other factors of each member shown in the drawings may be exaggerated to clarify the description.

<First Embodiment>

FIG. 1 is a block diagram showing a schematic configuration of a micropipette system 100 according to a first embodiment of the present disclosure.

The micropipette system 100 includes a micropipette 1, irradiation means 2 for irradiating an object with light, and control means 3 for controlling the range of an area irradiated with the light from the irradiation means 2, as shown in FIG. 1.

The micropipette 1 is an instrument for measuring a tiny volume of liquid on a micro-litter basis and includes a liquid-holding chamber 12 that holds a liquid for measurement sucked in by capillary action through an opening 11 provided at one end of the liquid-holding chamber 12. The micropipette 1 further includes an air releasing hole (not shown) for releasing air in the liquid-holding chamber 12 when a form for measurement is sucked.

The liquid-holding chamber 12 can be what is called a circular tube-shaped glass capillary. Markings (10 µl, 20 µl, and 30 µl) corresponding to quantitative volumes for measuring the liquid for measurement are provided on the outer surface of the liquid-holding chamber 12, as shown in FIG. 1. A photocatalyst layer 13 exhibiting a hydrophilic property at the time of light irradiation is formed on the inner surface (inside surface) of the liquid-holding chamber 12. The liquid-holding chamber 12 is not limited to the glass capillary described above, but may be any component that can suck the liquid for measurement in by capillary action. The liquid-holding chamber 12 can alternatively be made of, for example, a plastic material.

The opening 11 is provided at one end of the liquid-holding chamber 12 and serves as an inlet for sucking the liquid for measurement into the liquid-holding chamber 12 and an outlet for dispensing the non-quantitative liquid from the liquid-holding chamber 12. The inner diameter of the circular tube at the opening 11 is sized to be capable of sucking the liquid for measurement in by capillary action. The inner diameter can be, for example, 1 µm. Setting the inner diameter of the circular tube at the opening 11 at 1 µm or smaller allows the accuracy in measurement by using the micropipette 1 to be increased. The inner diameter of the circular tube at the opening 11 is, however, not limited to 1 µm, but may be any size that allows the liquid for measurement to be sucked in by capillary action, and can be, for example, several tens of micrometers.

The photocatalyst layer 13 is obtained by applying a photocatalyst on the inner surface of the liquid-holding chamber 12, and an example of the photocatalyst can be titanium dioxide ($TiO_2$). When the photocatalyst layer 13 is irradiated with ultraviolet light or any other suitable light, the photocatalyst is excited by the light and the surface of the photocatalyst layer 13 exhibits an excellent hydrophilic property, whereas the surface of the photocatalyst layer 13 exhibits a hydrophobic property when the light irradiation is terminated. The photocatalyst is not limited to titanium dioxide, but can be any other appropriate substance in accordance with the type of irradiation light.

A description will now be made of a method for manufacturing the micropipette 1 including the liquid-holding chamber 12 having the photocatalyst layer 13 formed on the inner surface thereof. The micropipette 1 can be manufactured, for example, by applying a photocatalyst onto a surface of a glass plate to form the photocatalyst layer 13, shaping the glass plate into a circular tube so that the inner surface works as the photocatalyst layer 13, and pulling the circular tube in the longitudinal direction of the glass plate to make it thin. A method for applying a photocatalyst onto a glass surface can be, for example, the method described in Japanese Patent Laid-Open No. 2008-142659.

Figure 2:
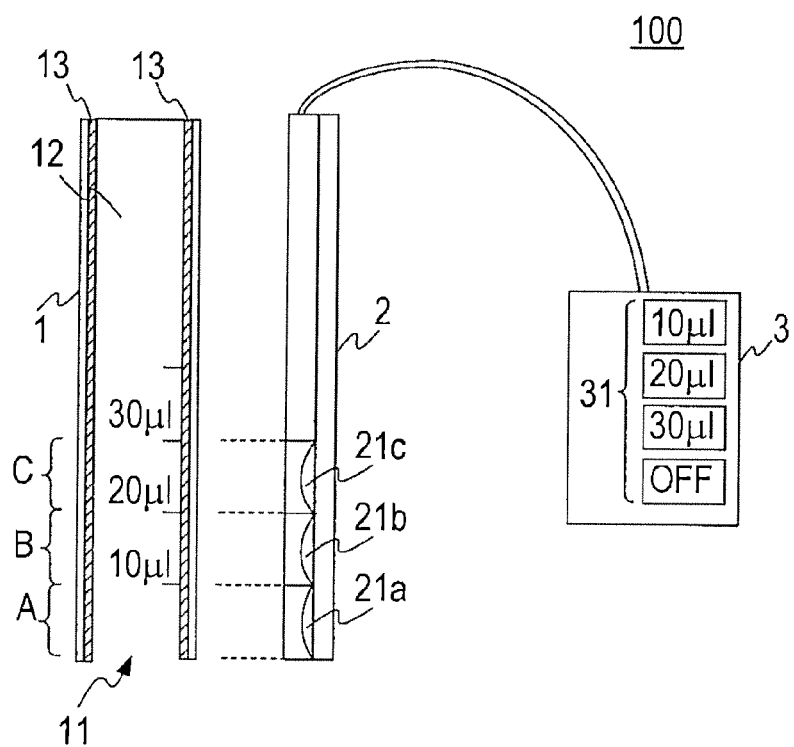
FIG. 2 is a schematic view showing how irradiation means 2 emits light in the first embodiment.

The irradiation means 2 is a light source that emits light toward the photocatalyst layer 13. The irradiation means 2 can be provided integrally with the micropipette 1 along the direction in which the liquid for measurement is sucked into the micropipette 1. A method for attaching the irradiation means 2 to the micropipette 1 can be any of a variety of methods, such as securing the two components with a band or a fastener. The irradiation means 2 includes a plurality of light sources 21a to 21c, as shown in FIG. 2. The plurality of light sources 21a to 21c are arranged in parallel to the direction in which the liquid for measurement is sucked into the micropipette 1, and emit ultraviolet light or any other suitable light toward areas A to C of the photocatalyst layer 13 that are disposed along the sucking direction. The areas A to C of the photocatalyst layer 13 correspond to the markings provided on the liquid-holding chamber 12. The light sources 21a to 21c are formed of, for example, laser light sources and emit light in the direction perpendicular to the longitudinal direction of the micropipette 1, whereby the area that exhibits a hydrophilic property and the area that exhibits a hydrophobic property on the photocatalyst layer 13 can be accurately distinguished from each other. While the number of light sources is three in the present embodiment, the number of light sources can be changed as appropriate, for example, in accordance with the quantitative volume of liquid for measurement.

The control means 3 controls the range of the area irradiated with the light from the irradiation means 2 in accordance with a desired quantitative volume of liquid for measurement, and is connected to the irradiation means 2 via a cable. That is, the control means 3 controls the range of the area irradiated with the light from the irradiation means 2 by causing a predetermined number of light sources of the plurality of light sources 21a to 21c, counting from the side where the opening 11 of the micropipette 1 is present, to emit light in accordance with a desired quantitative volume of liquid for measurement. For example, the control means 3 functions as switching means for turning the light sources 21a to 21c in the irradiation means 2 ON and OFF. When the desired quantitative volume is 10 µl, the user presses a switch 31 labeled with "10 µl" on the control means 3 to cause the light source 21a to emit light. When the desired quantitative volume is 20 µl, the user presses a switch 31 labeled with "20 µl" on the control means 3 to cause the light sources 21a and 21b to emit light. When the desired quantitative volume is 30 µl, the user presses a switch 31 labeled with "30 µl" on the control means 3 to cause the light sources 21a, 21b, and 21c to emit light. When the user presses a switch 31 labeled with "OFF" on the control means 3, the light sources 21a, 21b, and 21c stop emitting light. The control means 3 does not necessarily have the structure described above, but may have any other structure capable of controlling ON and OFF of the light sources 21a to 21c. Further, the control means 3 is not necessarily connected to the irradiation means 2 via a cable, but may be integrated with the micropipette 1 and the irradiation means 2.

A method for using the thus configured micropipette system 100 will be described below.

FIG. 3 is a flowchart showing the method for using the micropipette system 100 of the first embodiment.

First, the user operates the control means 3 to cause a predetermined light source to emit light in accordance with a desired quantitative volume of liquid for measurement (step S100). That is, for example, when the user wants to measure 20 μl of the liquid for measurement, the user presses the switch 31 labeled with "20 μl" on the control means 3 to cause the light sources 21a and 21b in the irradiation means 2 to emit light. When the light sources 21a and 21b emit light, the areas A and B of the photocatalyst layer 13 change their states from the hydrophobic state to the hydrophilic state. The user waits for a fixed period until the areas A and B of the photocatalyst layer 13 change their states to the hydrophilic state.

The user then puts the opening 11 of the micropipette 1 into the liquid for measurement with the photocatalyst layer 13 being irradiated with the light (step S101). When the opening 11 of the micropipette 1 is put into the liquid for measurement, the liquid for measurement is sucked through the opening 11 by capillary action and held in the liquid-holding chamber. In this process, the liquid for measurement is sucked through the opening 11 to the area of the photocatalyst layer 13 that exhibits the hydrophilic property, but does not reach the optical area that exhibits the hydrophobic property, whereby the sucking operation automatically stops.

The user then removes the opening 11 of the micropipette 1 out of the liquid for measurement (step S102).

To dispense the held liquid for measurement, the user operates the control means 3 to cause the light sources to stop emitting light (step S103). That is, the user presses the switch 31 labeled with "OFF" on the control means 3 to cause the light sources 21a and 21b in the irradiation means 2 to stop emitting light. When the light sources 21a and 21b stop emitting light, the areas A and B of the photocatalyst layer 13 change their states from the hydrophilic state to the hydrophobic state, and the liquid for measurement held in the liquid-holding chamber 11 is dispensed through the opening 11. The user may alternatively operate the control means 3, for example, to cause the light sources 21a and 21b to stop emitting light in a stepwise manner. In this case, the user can press the switch 31 labeled with "10 μl" on the control means 3 and subsequently press switch 31 labeled with "OFF" to dispense 10 μl of the liquid for measurement at a time.

As described above, according to the micropipette system 100 of the first embodiment, when the photocatalyst layer 13 formed on the inner surface of the liquid-holding chamber 11 is irradiated with light, the photocatalyst layer in the irradiated area changes its state to the hydrophilic state, and the liquid for measurement is automatically sucked to the area exhibiting the hydrophilic property. A desired quantitative volume of the liquid for measurement can thus be accurately sucked by controlling the range of the area irradiated with the light. Further, since the liquid for measurement automatically stops at the boundary between the area exhibiting the hydrophilic property and the area exhibiting the hydrophobic property, the user can stop the sucking without visually checking the quantitative volume.

Further, in the micropipette system 100, the photocatalyst can be stably excited with light, because the photocatalyst layer 13 can always be irradiated with uniform light from the irradiation means 2.

Moreover, in the micropipette system 100, the photocatalyst layer 13 can be irradiated with light more reliably by integrating the irradiation means 2 with the micropipette 1 along the direction in which the liquid for measurement is sucked into the micropipette 1.

<Second Embodiment>

A micropipette system 100' of a second embodiment includes light blocking means for blocking the light from the irradiation means.

The micropipette system 100' includes the micropipette 1, the irradiation means 2, light blocking means 4, and control means 5, as shown in FIG. 4. The components other than the light blocking means 4 and the control means 5 can be the same as those in the first embodiment, and no description of the same components will be made. It is, however, noted in the second embodiment that the irradiation means 2 does not necessarily include a plurality of light sources but may include, for example, a single light source.

The light blocking means 4 is disposed between the micropipette 1 and the irradiation means 2 and functions as a mask that blocks the light from the irradiation means 2 toward the photocatalyst layer 13. The light blocking means 4 is formed of, for example, a light blocking plate that blocks light and drive means (not shown) capable of translating the light blocking plate in the longitudinal direction of the micropipette 1. The light blocking means 4 can be provided, for example, integrally with the micropipette 1 along the direction in which the liquid for measurement is sucked into the micropipette 1. In this case, the light emitted from the irradiation means 2 toward the photocatalyst layer can be more reliably blocked.

The control means 5 controls the range over which the light blocking means 4 blocks light in accordance with a desired quantitative volume of non-quantitative liquid. The control means 5 controls the range over which the light from the irradiation means 2 is blocked by translating the light blocking plate in the longitudinal direction of the micropipette 1 in accordance with the desired quantitative volume of liquid for measurement. For example, when the desired quantitative volume is 10 μl, the user presses a switch 51 labeled with "10 μl" on the control means 5, and the drive means translates the light blocking plate in such a way that it covers the areas B and C of the photocatalyst layer. When the desired quantitative volume is 20 μl, the user presses a switch 51 labeled with "20 μl" on the control means 5, and the drive means translates the light blocking plate in such a way that it covers the area C of the photocatalyst layer. When the desired quantitative volume is 30 μl, the user presses a switch 51 labeled with "30 μl" on the control means 5, and the drive means translates the light blocking plate in such a way that it covers the area other than the areas A, B, and C of the photocatalyst layer. When the user presses a switch 51 labeled with "OFF" on the control means 5, the light blocking plate is moved to cover all the areas A, B, and C. It is noted that the control means 5 does not necessarily have the structure described above, but may have any other structure capable of controlling the movement of the light blocking plate.

A method for using the thus configured micropipette system 100' will be described below.

FIG. 5 is a flowchart showing the method for using the micropipette system 100' of the second embodiment. It is assumed in the following processes that at least the measurement areas A, B, and C of the photocatalyst layer 13 are irradiated with the light from the irradiation means 2.

The user first operates the control means 5 to block the light toward the photocatalyst layer 13 in accordance with a desired quantitative volume of liquid for measurement (step S200). That is, when the user wants to measure, for example, 20 μl of liquid for measurement, the user presses the switch 51 labeled with "20 μl" on the control means 5 so that the light blocking plate blocks the light toward the area C of the photocatalyst layer 13. The user waits for a fixed period until the areas A and B of the photocatalyst layer 13 change their states to the hydrophilic state after the light toward the area C of the photocatalyst layer is blocked and the areas A and B of the photocatalyst layer 13 are irradiated with the light.

The processes S201 to S203 can be the same as the processes S101 to S103 in the first embodiment, and no description of the processes S201 to S203 will be made.

As described above, according to the micropipette system 100' of the second embodiment, using the light blocking means 4 to completely block the light toward the area of the photocatalyst layer 13 that should not be irradiated with the light, in addition to the advantageous effect provided in the micropipette system 100 of the first embodiment, allows the boundary between the area exhibiting the hydrophilic property and the area exhibiting the hydrophobic property to be clearly defined, whereby more precise measurement can be performed.

<Variation 1>

While the preferred embodiments of the present disclosure have been described above, the present disclosure should not be limited thereto, and a variety of changes, additions, and omissions can be made by those skilled in the art without departing from the spirit and scope set forth in the claims.

For example, unlike the above embodiments, the irradiation means 2 is not necessarily provided in the present disclosure, but sunlight or light from fluorescent lights in a room can be used. In this case, a variety of methods can be used to form an area over which light is blocked in accordance with a quantitative volume of liquid for measurement, for example, attaching an opaque cap to the micropipette 1 or wrapping a black tape around the micropipette 1.

<Variation 2>

While the above embodiments have been described with reference to the case where the micropipette 1 and the irradiation means 2 are integrally provided, the present disclosure is not limited thereto. The micropipette 1 and the irradiation means 2 can alternatively be disposed separately if a light source used in the irradiation means 2 emits directional light. Further, the irradiation means 2 does not necessarily include the plurality of light sources described above. For example, a single light source can be used, and the width of the area irradiated with the light from the light source can be adjusted in the longitudinal direction of the micropipette 1 in accordance with a desired quantitative volume of liquid for measurement.

<Variation 3>

While the above embodiments have been described with reference to the case where the liquid-holding chamber 12 has a circular tube-shaped structure, the present disclosure is not limited thereto. For example, the liquid-holding chamber 12 can have a rectangular tube-shaped structure. The rectangular tube-shaped liquid-holding chamber can, for example, have a structure in which two glass plates each of which has a photocatalyst layer formed on at least one of the surfaces thereof are assembled in such a way that the surfaces on which the photocatalyst layer is formed face each other with a predetermined gap therebetween and at least one end of the assembled two glass plates has an opening. In this case, the liquid-holding chamber 12 can be produced with the gap between the two glass plates being uniform by disposing uniform nano-particles between the two glass plates when they are assembled. The uniform nano-particles can be, for example, those described in Japanese Patent Laid-Open No. 2004-070101.

<Variation 4>

While the above embodiments have been described with reference to the case where the photocatalyst layer is formed on the inner surface of the liquid-holding chamber 12, the present disclosure is not limited thereto. For example, glass containing a component mixed with a photocatalyst can be used as the material that forms the liquid-holding chamber 12 so that the liquid-holding chamber 12 itself has the feature of the photocatalyst layer 13.

<Variation 5>

While the above embodiments have been described with reference to the case where the markings corresponding to quantitative volumes are provided on the outer surface of the liquid-holding chamber 12, the markings are not necessarily provided. For example, a liquid for measurement can be accurately measured by establishing in advance the relationship between the amount of controlling the irradiation means or the light blocking means and the volume measured by the micropipette 1.

The invention claimed is:

1. A micropipette system comprising:
a micropipette including a liquid-holding chamber that holds a liquid for measurement sucked in by capillary action through an opening provided at an end of the liquid-holding chamber, the liquid-holding chamber having an inner surface on which a photocatalyst layer is formed, the photocatalyst changing from a hydrophobic state to a hydrophilic state when irradiated and extending along the inner surface to the opening; and
a switch configured to control irradiation of at least one of a first area and a second area of the photocatalyst layer with light in accordance with a desired quantitative volume of the liquid for measurement, the desired quantitative volume of the liquid for measurement corresponding to the at least one of the first area and the second area of the photocatalyst layer.

2. The micropipette system according to claim 1, further comprising a light source configured to emit light toward the photocatalyst layer.

3. The micropipette system according to claim 2, wherein the light source is provided integrally with the micropipette along the direction in which the liquid for measurement is sucked into the micropipette.

4. The micropipette system according to claim 1, wherein the liquid-holding chamber has a circular tube-shaped structure in which the photocatalyst layer is formed along the inner-diameter surface of the liquid-holding chamber and an end of the liquid-holding chamber is open as the opening.

5. The micropipette system according to claim 1, wherein the liquid-holding chamber has a rectangular tube-shaped structure in which the photocatalyst layer is formed along the inner surface of the liquid-holding chamber and an end of the liquid-holding chamber is open as the opening.

6. A micropipette system comprising:
a micropipette including a liquid-holding chamber that holds a liquid for measurement sucked in by capillary action through an opening provided at an end of the liquid-holding chamber, the liquid-holding chamber having an inner surface on which a photocatalyst layer is formed, the photocatalyst changing from a hydrophobic state to a hydrophilic state when irradiated and extending along the inner surface to the opening;
a light blocking plate configured to block light toward a first area and a second area of the photocatalyst layer; and
a switch configured to control the range over which irradiation of at least one of the first area and the second area of the photocatalyst layer by the light blocking plate blocks light in accordance with a desired quantitative volume of the liquid for measurement, the desired quantitative volume of the liquid for measurement corresponding to the at least one of the first area and the second area of the photocatalyst layer.

7. A method for using a micropipette system which has:
a micropipette including a liquid-holding chamber that holds a liquid for measurement sucked in by capillary action through an opening provided at an end of the liquid-holding chamber, the liquid-holding chamber having an inner surface on which a photocatalyst layer is formed, the photocatalyst changing from a hydrophobic state to a hydrophilic state when irradiated and extending along the inner surface to the opening; and
a switch configured to control the range over which irradiation of a first area and a second area of the photocatalyst layer is irradiated with light, the method comprising:
controlling the range over which irradiation of at least one of the first area and the second area of the photocatalyst layer is irradiated with light in accordance with a desired quantitative volume of the liquid for measurement, the desired quantitative volume of the liquid for measurement corresponding to the at least one of the first area and the second area of the photocatalyst layer.

* * * * *

UNITED STATES PATENT AND TRADEMARK OFFICE
CERTIFICATE OF CORRECTION

PATENT NO.         : 8,232,111 B2
APPLICATION NO.    : 12/665434
DATED              : July 31, 2012
INVENTOR(S)        : Kusuura Page 1 of 1

It is certified that error appears in the above-identified patent and that said Letters Patent is hereby corrected as shown below:

On the Title Page, in Item (56), under "FOREIGN PATENT DOCUMENTS", in Column 1, Line 1, delete "JP 05-184949 7/1993".

On the Title Page, in Item (56), under "FOREIGN PATENT DOCUMENTS", in Column 1, Line 3, delete "JP 2004-070101 3/2004".

On the Title Page, in Item (56), under "OTHER PUBLICATIONS", in Column 2, Line 11, delete "Minaturized" and insert -- Miniaturized --, therefor.

On Title Page 2, in Item (56), under "OTHER PUBLICATIONS", in Column 1,
Line 5, delete "2009." and insert -- 2009 (English translation not readily available). --, therefor.

On Title Page 2, in Item (56), under "OTHER PUBLICATIONS", in Column 1, Line 7, delete "(English translation not readily available)." and insert -- (With English translation). --, therefor.

Signed and Sealed this
Twenty-third Day of April, 2013

Teresa Stanek Rea
*Acting Director of the United States Patent and Trademark Office*